(12) United States Patent
Allen et al.

(10) Patent No.: US 8,927,239 B2
(45) Date of Patent: Jan. 6, 2015

(54) PROCESS FOR IMPROVING THE YIELD AND EFFICIENCY OF AN ETHANOL FERMENTATION PLANT

(75) Inventors: Stephen D. Allen, Eagle, ID (US); Michael R. Rusnack, Star, ID (US)

(73) Assignee: Water Solutions, Inc., Sioux Falls, SD (US)

( * ) Notice: Subject to any disclaimer, the term of this patent is extended or adjusted under 35 U.S.C. 154(b) by 1442 days.

(21) Appl. No.: 12/030,578

(22) Filed: Feb. 13, 2008

(65) Prior Publication Data

US 2008/0193991 A1   Aug. 14, 2008

Related U.S. Application Data

(60) Provisional application No. 60/889,644, filed on Feb. 13, 2007, provisional application No. 60/955,282, filed on Aug. 10, 2007.

(51) Int. Cl.
*C12P 7/08* (2006.01)
*C12P 7/10* (2006.01)

(52) U.S. Cl.
CPC .. *C12P 7/10* (2013.01); *Y02E 50/16* (2013.01); *Y02E 50/17* (2013.01)
USPC .......................................... 435/161; 435/163

(58) Field of Classification Search
CPC ......... B01D 61/022; C12P 7/10; C12M 21/04
USPC ....................................................... 435/161
See application file for complete search history.

(56) References Cited

U.S. PATENT DOCUMENTS

| | | | |
|---|---|---|---|
| 7,497,955 B2* | 3/2009 | Scheimann et al. | 210/709 |
| 2004/0063184 A1* | 4/2004 | Grichko | 435/161 |
| 2005/0164355 A1* | 7/2005 | Vlasenko et al. | 435/101 |
| 2007/0036881 A1* | 2/2007 | Griffith | 426/11 |
| 2007/0141691 A1* | 6/2007 | Hirl | 435/161 |
| 2007/0199894 A1* | 8/2007 | Peyton et al. | 210/603 |
| 2007/0249029 A1* | 10/2007 | Marshall et al. | 435/161 |
| 2007/0281344 A1* | 12/2007 | Lantero et al. | 435/161 |
| 2008/0227166 A1* | 9/2008 | Allain et al. | 435/161 |

OTHER PUBLICATIONS

Baez-Smith, Anaerobic digestion of vinasse for the production of methane in the sugar cane distillery, 2006 SPRI Conference on Sugar processing, p. 268-287.*

Wilkie et al., Stillage characterization and anaerobic treatment of ethanol stillage from conventional and cellulosic feedstocks, Biomass and Bioenergy, vol. 19, 2000, p. 63-102.*

* cited by examiner

*Primary Examiner* — Taeyoon Kim
*Assistant Examiner* — Tiffany Gough
(74) *Attorney, Agent, or Firm* — Kirton McConkie; Evan R. Witt

(57) ABSTRACT

A process for improving the yield and efficiency of an ethanol fermentation plant that receives organic fermentable feedstock material, prepares the feedstock for fermentation, ferments the feedstock with yeast to produce ethanol, and produces stillage as a byproduct of ethanol fermentation. The process steps which can be operated independently or in combination, may include, but are not limited to, degrading fatty acids in the fermentable feedstock material prior to fermentation; degrading cellulose and hemicellulose present in the feedstock prior to fermentation; adding a surfactant to the fermentable feedstock; separating a liquid fraction from the stillage; recycling the liquid fraction to be combined with the fermentable feedstock; recovering a solid fraction from the stillage; and introducing at least a portion of the solid fraction to an anaerobic digester to produce methane.

20 Claims, 6 Drawing Sheets

PROCESS FOR IMPROVING THE YIELD AND EFFICIENCY OF AN ETHANOL FERMENTATION PLANT

CROSS-REFERENCE TO RELATED APPLICATIONS

This application claims the benefit of U.S. Provisional Patent Application Ser. No. 60/955,282, filed Aug. 10, 2007 and U.S. Provisional Patent Application Ser. No. 60/889,644, filed Feb. 13, 2007, which applications are incorporated by reference.

BACKGROUND OF THE INVENTION

This invention relates to a process for improving ethanol yield and operating efficiency in an ethanol fermentation process. The process includes several steps which can be operated independently or in combination to optimize the ethanol fermentation process. Some of the steps include, but are not limited to, pre-fermentation fatty acid destruction, surfactant addition to enhance enzyme activity, thin stillage water separation and recycling, and use of anaerobic digestion of solids.

Ethanol fermentation is the biological process by which sugars such as glucose, fructose, and sucrose, are converted into ethanol and carbon dioxide. Yeasts carry out ethanol fermentation on sugars in the absence of oxygen. Because the process does not require oxygen, ethanol fermentation is classified as anaerobic. Ethanol fermentation is responsible for the production of ethanol in alcoholic beverages and for much of the production of ethanol for use as fuel.

The three basic types of fermentable plant-based feedstock are saccharine (sugar containing) materials, starchy materials, and cellulose materials. Saccharine materials contain simple, directly fermentable six and twelve carbon sugar molecules such as glucose, fructose, and maltose. Such materials include sugar cane, sugar beets, fruit, citrus molasses, cane sorghum, whey and skim milk. Starchy materials contain more complex carbohydrates such as starch and inulin that can be broken down into the simpler six and twelve carbon sugars by hydrolysis with acid or by the action of enzymes in a process called malting. Such materials include corn, grain sorghum, barley, wheat, rice, potatoes, sweet potatoes, and so on. Cellulose materials, such as wood, wood waste, paper, straw, corn stalks, corn cobs, cotton, etc., contain material that can be hydrolyzed with acid, enzymes or otherwise converted into fermentable sugars called glucose.

Manufacturing ethanol from saccharine feedstocks generally requires: extraction or crushing to make the sugars available to the yeast enzymes during fermentation; dilution, which is only required with certain materials; fermentation; and distillation. Starchy materials require the steps of: milling to free the starchy material from, for example, grain kernels; dilution; cooking to dissolve and "gelatinize" the starch; and conversion of the starch to fermentable sugars by malting, enzymes, or acid hydrolysis in addition to the steps of fermentation and distillation. Cellulose materials are similar to starchy materials in that they must be converted to fermentable carbohydrates prior to fermentation.

In the United States, the main feedstock for the production of ethanol is currently corn. Approximately 2.8 gallons of ethanol are produced from one bushel of corn (0.42 liter per kilogram). While much of the corn turns into ethanol, some of the corn also yields by-products such as DDGS (distillers dried grains with solubles) that can be used to fulfill a portion of the diet of livestock. A bushel of corn produces about 18 pounds of DDGS. Although most of the fermentation plants have been built in corn-producing regions, other feedstocks may be used, including by not limited to sorghum and pearl millet.

FIG. 1A is a block diagram of a typical ethanol plant utilizing a dry milling process 10. It will be understood that this process may be used with a variety of feedstocks, including the feedstocks mentioned above. FIG. 1B is a schematic representation of process equipment to perform the ethanol fermentation process of FIG. 1A. The major steps are outlined below.

The feedstock milling 12 may be performed using hammer mills or other milling means known in the art, which grind it into a fine powder called meal 14. The feedstock may be corn, barley, wheat, or other feedstock mentioned above. The meal 14 is prepared into a mash suitable for fermentation. Mash preparation 16 may include mixing the meal with water to form the mash. Enzymes 18 are added to convert starch into fermentable sugars, a process called saccharification. Ammonia 20 may be added for pH control and as a nutrient to the yeast. The prepared mash 22 is processed in a high-temperature cooker to reduce bacteria levels ahead of fermentation. The mash is cooled and transferred to one or more fermenters for fermentation 24. Yeast is added to the mash to ferment the sugars to ethanol and carbon dioxide 26. Carbon dioxide 26 is given off in great quantities during fermentation. Many ethanol plants collect the carbon dioxide, clean it of any residual alcohol, compress it and sell it for use to carbonate beverages or in the flash freezing of meat. Using a continuous process, the fermenting mash will be allowed to flow, or cascade, through several fermenters until the mash is fully fermented and then leaves the final tank. In a batch fermentation process, the mash stays in one fermenter for about 48 hours before the distillation process is started.

After fermentation, the resulting "beer" 28 is transferred to distillation columns where distillation 30 separates the ethanol 32 from the remaining "stillage" 34. The stillage 34 contains non-fermentable solids from the feedstock and the yeast cells. The ethanol 32 undergoes dehydration 36 in a molecular sieve system to form approximately 200 proof (anhydrous) ethanol 38.

The stillage 34, also referred to as whole stillage, undergoes centrifugation 40 to separate wet distillers grain 42 from thin stillage 44. The wet distillers grain 42 includes the course grain and is typically dried to form dried distillers grains. Distillers grains, wet and dried, are high in protein and other nutrients and are a highly valued livestock feed ingredient. The thin stillage 44 includes solubles, and some ethanol plants use evaporation 46 to remove water from the thin stillage 44 to create a "syrup" containing Condensed Distillers Solubles (CDS) that can be a separate production product. The coarse grain and the syrup may be combined and dried together in a dryer 50 to produce dried distillers grains with solubles (DDGS) 52, a high quality, nutritious livestock feed.

A water condensate 54 from the evaporators 46 may be recovered and recycled in the process.

Many fermentable plant-based feedstocks contain oils that consist principally of triglycerides (also known as triglycerols). Triglycerides are fatty acid esters of glycerol. The fatty acids have various compositions depending on the plant source. For example, corn oil contains about 99% triacylglycerides, which include approximately 59% polyunsaturated fatty acid, 24% monounsaturated fatty acid, and 13% saturated fatty acid. Some of the more common fatty acids present in corn oil include palmitic, stearic, oleic, and linoleic acid.

While the use of stillage in animal feed applications is desirable, stillage contains high quantities of fatty acids that limit its usefulness as an animal feed. Presently, stillage can only represent a small fraction of the diet of livestock and poultry. For example, dairy cows can only consume from about 4 to 8 pounds of stillage per day per cow. It would be a significant advancement in the art to reduce the quantity of fatty acids present in stillage to render it more usable as an animal feed and in other post-fermentation applications.

Feedstock materials used in ethanol fermentation processes often contain complex carbohydrates that are not fermentable under current ethanol fermentation processes. It would be an advancement in the art to provide means for fermenting more carbohydrates present in feedstock materials.

BRIEF SUMMARY OF THE INVENTION

In accordance with the present invention, there is disclosed herein a process for improving ethanol yield and operating efficiency in an ethanol fermentation process. Embodiments within the scope of the invention include process steps which can be operated independently or in combination to optimize the ethanol fermentation process. Some of the steps include, but are not limited to:

The elimination of fatty acids, specifically, C-16:0, C-18:0, C-18:1, C-18:2, C-18:3, and C-20:0, from the solid and liquid fraction of the whole or thin stillage. This is preferably accomplished before the fermentation step. Fatty acid destruction greatly improves the value of stillage for post-fermentation uses, including but not limited to, animal feed and anaerobic digestion. The elimination of fatty acids also enables the use of specific enzymes for the hydrolysis of hemicellulose, cellulose, pentosans, and oligosaccharides (more commonly known as non-digestibles) prior to fermentation. This produces more fermentable sugars which directly improves the yield and efficiency of the ethanol fermentation process.

The use of one or more surfactants or surface active agents to reduce viscosity and improve penetrability of solids and semi-solids in the pre-fermentation of the feedstock mash. Without being bound by theory, it is believed surfactants or surface active agents act to improve activity of enzymes (pre-fermentation) and of yeast during fermentation due to improved mass transfer and access of the enzyme to the substrate and of the yeast to fermentable sugars. In addition, it is believed the reduced osmotic pressure increases the maximum concentration of ethanol that can be produced during fermentation which further improves the yield and efficiency of the ethanol fermentation process.

The reuse of the heated water from the separation of the whole or thin stillage and the reuse of that heated water as the feedstock to the front end where it is mixed with enzymes and feed materials for the fermentation portion of the ethanol generation. The recycling of heated water reduces energy requirements for the process and it reduces the water fresh water requirements.

The use of wet distillers grain or the solid fraction of thin stillage as feed to an anaerobic biodigester. A biodigester can produce methane which can be used to generate electricity and heat for use in the ethanol fermentation process. Post anaerobic biodigestion solids may be available for addition as dried distillers grains (DDG's) if desired.

The foregoing improvements to the process of ethanol fermentation may be used separately or in combination as desired. It will be appreciated that implementation of some or all of the foregoing process improvements may provide significant savings on energy and improve the yield of ethanol produced. Both have an enormous financial impact on ethanol generation in the world. In addition, the destruction of fatty acids greatly improves the value and usefulness of the stillage produced during ethanol fermentation.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment, but may refer to every embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, specific details are given to provide a thorough understanding of embodiments of the invention. One skilled in the relevant art will recognize, however, that the invention may be practiced without one or more of the specific details or method steps, or with other methods, components, materials, and so forth. In other instances, well-known structures, materials, or operations are not shown or described in detail to avoid obscuring aspects of the invention.

The embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the improvements to ethanol fermentation processes within the scope of the present invention as disclosed herein and represented in the Figures, is not intended to limit the scope of the invention, as claimed, but is merely representative of possible embodiments within the scope of the invention.

Figure 1A:
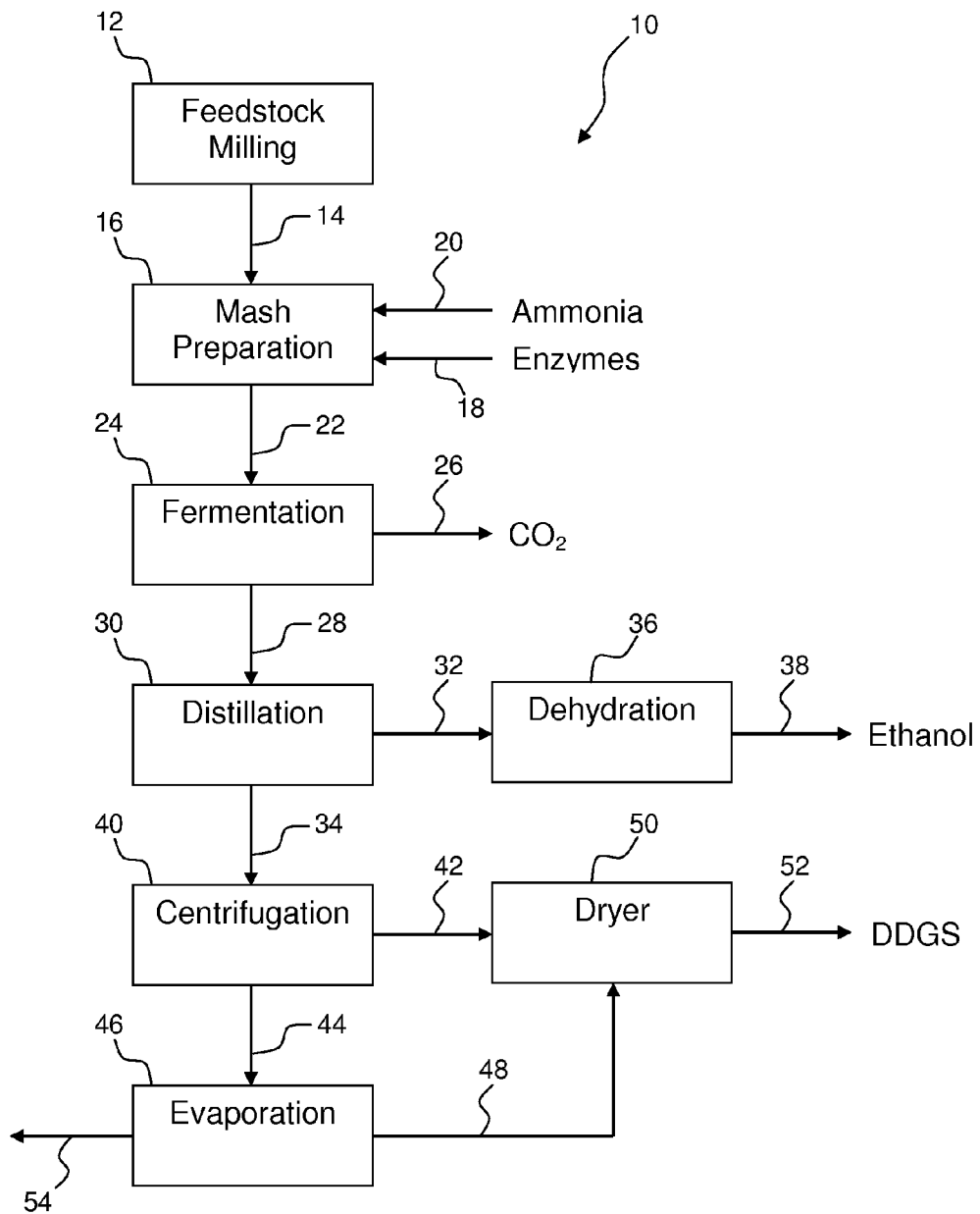
FIG. 1A is a schematic block diagram of an ethanol fermentation process.
Figure 1B:
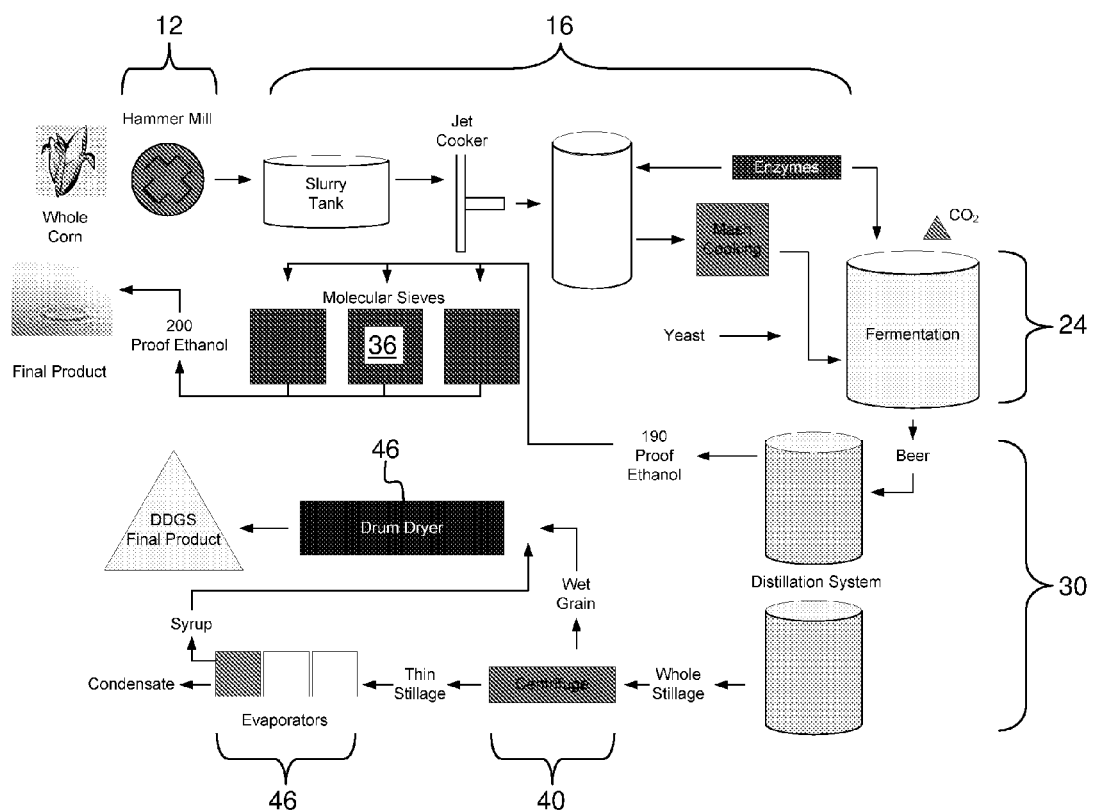
FIG. 1B is a schematic representation of process equipment to perform the ethanol fermentation process of FIG. 1A.
Figure 2:
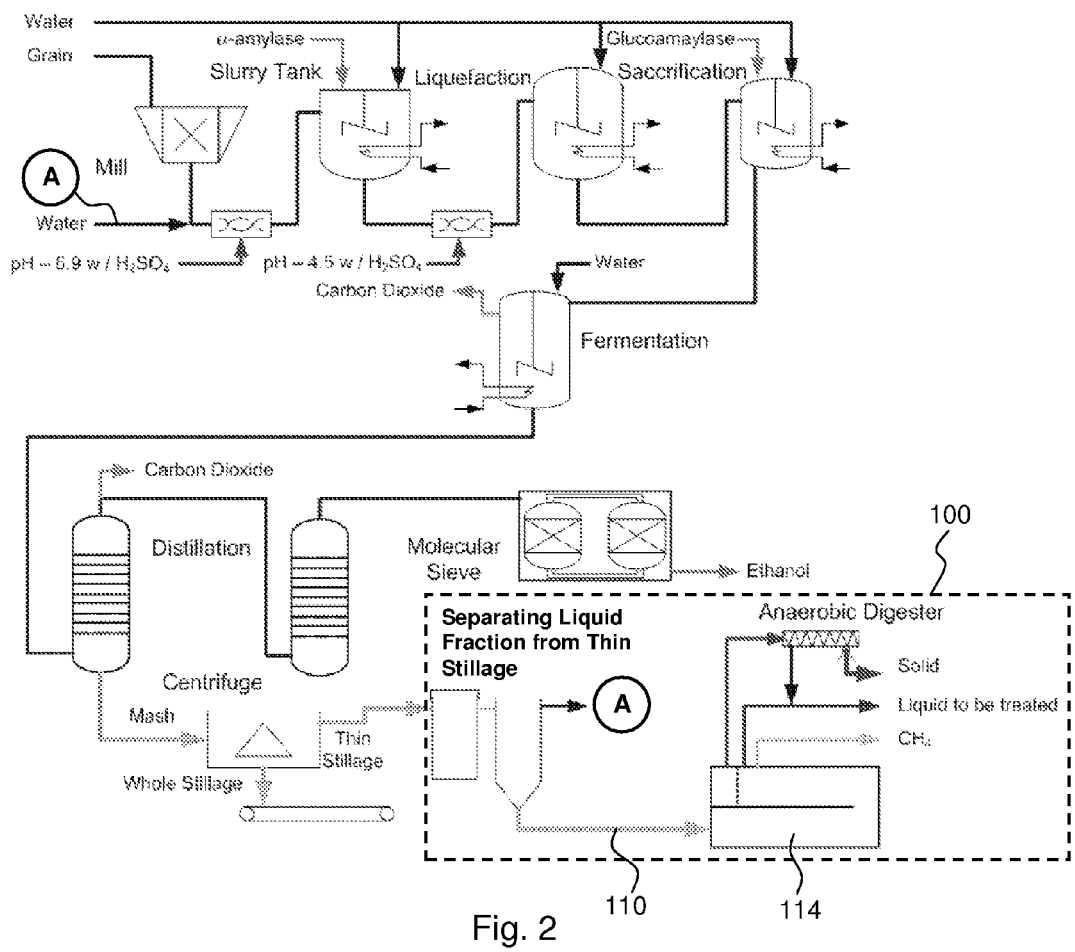
FIG. 2 is a schematic representation of process equipment to perform ethanol fermentation and post-fermentation treatment of thin stillage within the scope of the invention.

Referring to FIG. 2, which is a schematic representation of process equipment to perform ethanol fermentation and post-fermentation treatment of thin stillage within the scope of the invention. The post-fermentation treatment of thin stillage, represented generally by the dashed box 100, includes separation of the liquid fraction from thin stillage. It also may include anaerobic digestion of the solids.

Following fermentation and distillation, the stillage is typically centrifuged to separate wet distillers grain from thin stillage. In current ethanol fermentation processes, described above, the thin stillage is typically evaporated to form a "syrup." Instead of evaporating the thin stillage, the post-fermentation treatment of thin stillage shown in box 100 of FIG. 2 includes separation of the liquid fraction from the thin stillage. The separation process disclosed herein may be used with wet distillers grain and thin stillage, but thin stillage is preferred. In the separation process, the thin stillage is adjusted to a pH of approximately 6.0-8.5, with a pH of about 7 being presently preferred. This may be accomplished by adding a suitable base, such as, but not limited to, magnesium hydroxide or calcium oxide. Once a suitable pH is achieved, a high molecular weight, high anionic charge organic polymer is preferably added. Polyacrylamide is one example of an anionic organic polymer that may be used. The polymer molecular weight is preferably in range of about 8 to 25 million, and more preferably in the range of about 18 to 20 million. The polymer preferably has from about 25 to 50 mole percent anionic charge. The polymer used is preferably non-toxic to livestock and poultry or Generally Recognized As Safe (GRAS), such that recovered solids may be used as an animal feed material. Solids are formed from this reaction and are capable of rapid settling and complete separation of the liquid and solid phases of the stillage. Two results of this separation are 1) the pH of the liquid fraction of the separation is about pH 5.0-5.3, and the solids are about pH 7.1-7.4, and 2) the reaction takes out most contaminants from the liquid phase.

Figure 3A:
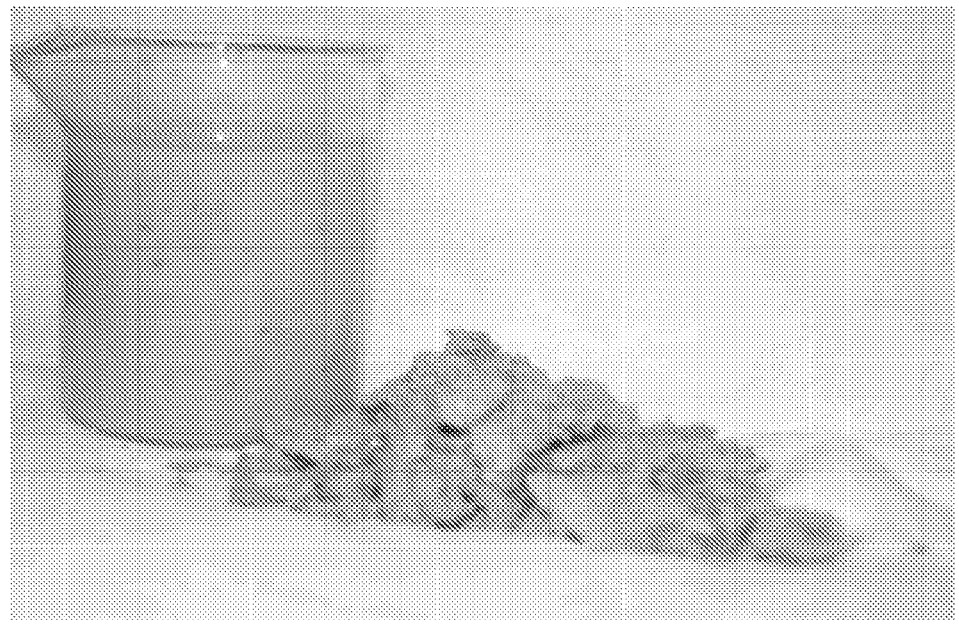
FIG. 3A is a photo of thin stillage before treatment to separate the liquid phase.
Figure 3B:
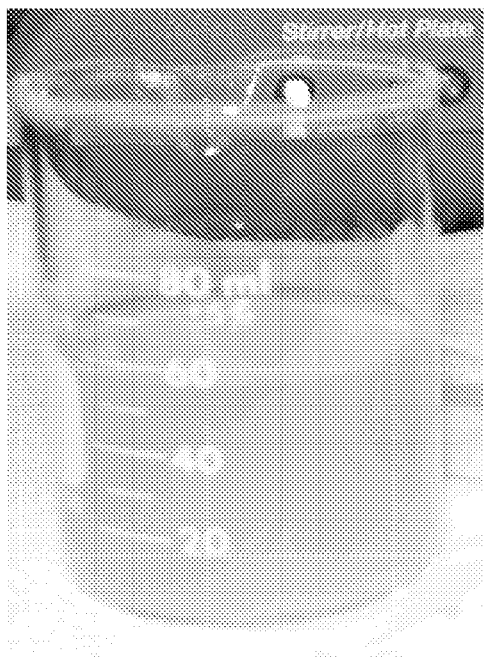
FIG. 3B is a photo of the liquid phase separated from the thin stillage.

FIG. 3A is a photo of thin stillage before treatment and air dried solids separated from the thin stillage. FIG. 3B is a photo of the liquid phase separated from the thin stillage of FIG. 3A.

This process is very robust and the findings are reproducible. Pilot scale testing has been carried out employing Utica Energy thin stillage at Holsum Dairy. The testing has also been carried out at SELC (SiouxLand Energy and Livestock Corporation). Other laboratory tests have been carried out on Utica Energy prior to the pilot scale testing.

Tables 1A and 1B, below, report analysis of the liquid phase of the thin stillage, pre- and post-separation.

TABLE 1A

Metals Analysis

| | Raw (ppb) | Treated (ppb) | Reduction |
|---|---|---|---|
| Aluminum, Al | 876 | 884 | −0.91% |
| Antimony, Sb | <500 | <100 | 80.00% |
| Arsenic, As | <500 | 152 | 69.60% |
| Barium, Ba | <250 | 121 | 51.60% |
| Beryllium, Be | <25 | <10 | 60.00% |
| Boron, B | 2,430 | 318 | 86.91% |
| Cadmium, Cd | <25 | <5 | 80.00% |
| Calcium, Ca | 59,000 | 99,000 | −67.80% |
| Chromium, Cr | <250 | <50 | 80.00% |
| Cobalt, Co | <100 | <20 | 80.00% |
| Copper, Cu | 2,140 | 78 | 96.36% |
| Iron, Fe | 10,200 | 484 | 95.25% |
| Lead, Pb | <250 | <50 | 80.00% |
| Magnesium, Mg | 852,000 | 951,000 | −11.62% |
| Manganese, Mn | 4,460 | 170 | 96.19% |
| Molybdenum, Mo | <250 | 96 | 61.60% |
| Nickel, Ni | <100 | 88 | 12.00% |
| Potassium, K | 2,930,000 | 1,230,000 | 58.02% |
| Selenium, Se | <500 | 323 | 35.40% |
| Silicon, Si | 11,000 | 11,600 | −5.45% |
| Sodium, Na | 63,500 | 311,000 | −389.76% |
| Thallium, Tl | <500 | <100 | 80.00% |
| Titanium, Ti | <500 | <100 | 80.00% |
| Vanadium, V | <250 | <50 | 80.00% |
| Zinc, Zn | 12,800 | 31.0 | 99.76% |

TABLE 1B

Other Analcites

| | Raw (ppm) | Treated (ppm) | Reduction |
|---|---|---|---|
| Nitrate (as N) | 39 | 1 | 97.4% |
| Ortho Phosphate (as P) | 720 | 6 | 99.13% |
| Total Phosphate (as P) | 1,650 | 168 | 89.82% |
| Chloride, Cl | 434 | 193 | 55.53% |
| Fluoride, F | 1,090 | 552 | 49.36% |
| Sulfate, $SO_4$ | 1,630 | 1,690 | −3.68% |
| Carbon, Total Organic, TOC | 40,308 | 7,349 | 81.77% |
| Total Dissolved Solids, TDS | 37,300 | 11,900 | 68.10% |
| pH | 3.15 | 5.0–5.27 | |
| Temperature | 148°F. | 148° F. | |
| Total Suspended Solids, TSS | 42,800 | 518 | 98.77% |
| Total Nitrogen, TKN | 2,510 | 388 | 84.54% |
| Biochemical Demand | 18,500 | 6,110 | 66.97% |

The thin stillage influent solids concentration, as total suspended solids (or TSS), was approximately 40,000 to 50,000 milligrams per liter (mg/L). The effluent from the process was 700 mg/L or less. The elimination of total dissolved solids (TDS) was also an intended consequence of this reaction, eliminating in a typical range of 70-85% of the TDS from the solution; the TDS co-precipitated to the solids. The optimum reaction sequence above, and a final pH of 7.0-7.4, appear to maximize the TDS elimination; a typical reduction was 85%.

The reactions involved in separating the liquid phase from the thin stillage are preferably carried out at 60-74° C. (140-165° F.). This temperature is a useful temperature recycling the liquid phase. As depicted in FIG. 2, the liquid phase "A" may be recycled and used as input water in the process. The solids 110 may be sent to an anaerobic digester 114, combined with the wet distillers grain, or used independently as animal feed due to its high nutritional content.

The recycled liquid from the stillage separation, liquid phase "A", is at elevated process fermentation temperature, has a pH consistent with addition of enzymes, and contains no contaminants that could/would poison the enzymes when employed on the front end of the process. Without any further processing or additions, this liquid fraction may be employed as dilution for the dry milled feedstock addition and as such would save money in heat required to bring the water to temperature. In addition, the liquid fraction has some required nutrients desired for fermentation.

The addition of enzymes has several possible iterations, including but not limited to, the addition of a lipase, designed to reduce or eliminate the fatty acid portion of the milled corn, or other feedstock, prior to fermentation. Our testing shows that post-fermentation destruction of fatty acid is incomplete. For example, a given initial dose of lipase enzyme to the post-fermentation stillage destroyed no more than 20% of the fatty acids. Increasing the dosage by three times the initial amount resulted in approximately 35% destruction of fatty acids. While adding even more enzymes might destroy more fatty acids, the cost becomes prohibitive. However, the findings of our testing show that the addition of the same initial dose of lipase before the fermentation process destructs the fatty acid portion of the corn to 75-95% of all the fatty acids present.

Figure 4A:
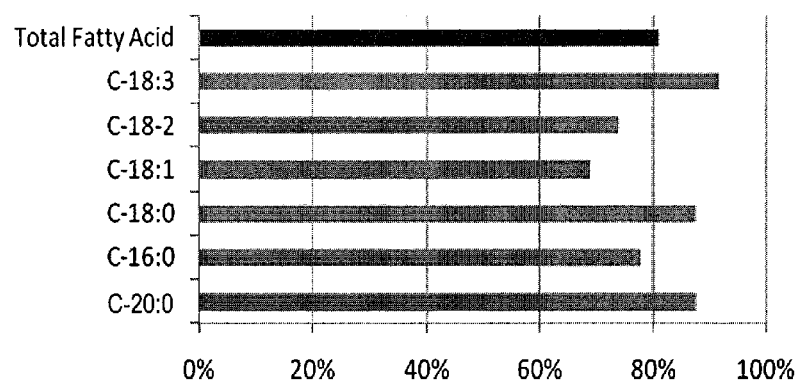
FIG. 4A is a graph of fatty acid destruction percentage in corn feedstock achieved through the use of pre-fermentation lipase enzymes.
Figure 4B:
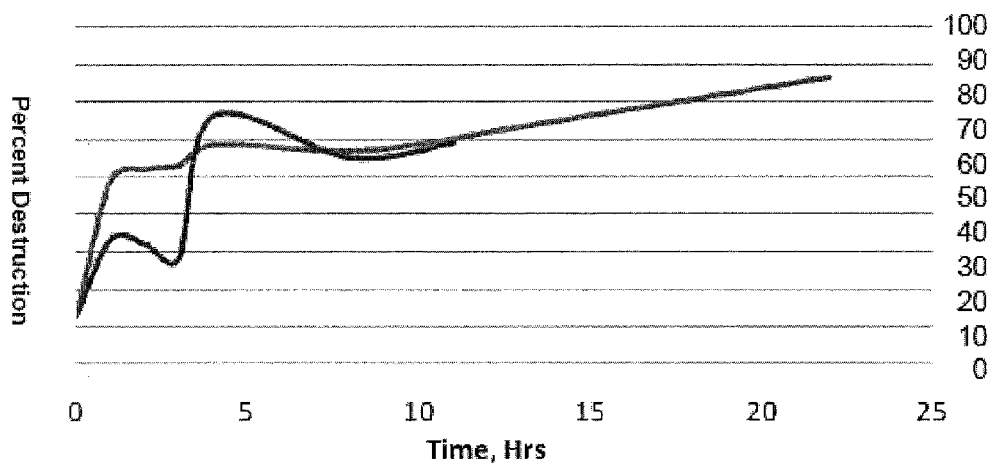
FIG. 4B is a graph of fatty acid destruction in corn feedstock as a function of time achieved through the use of pre-fermentation lipase enzymes.
Figure 5:
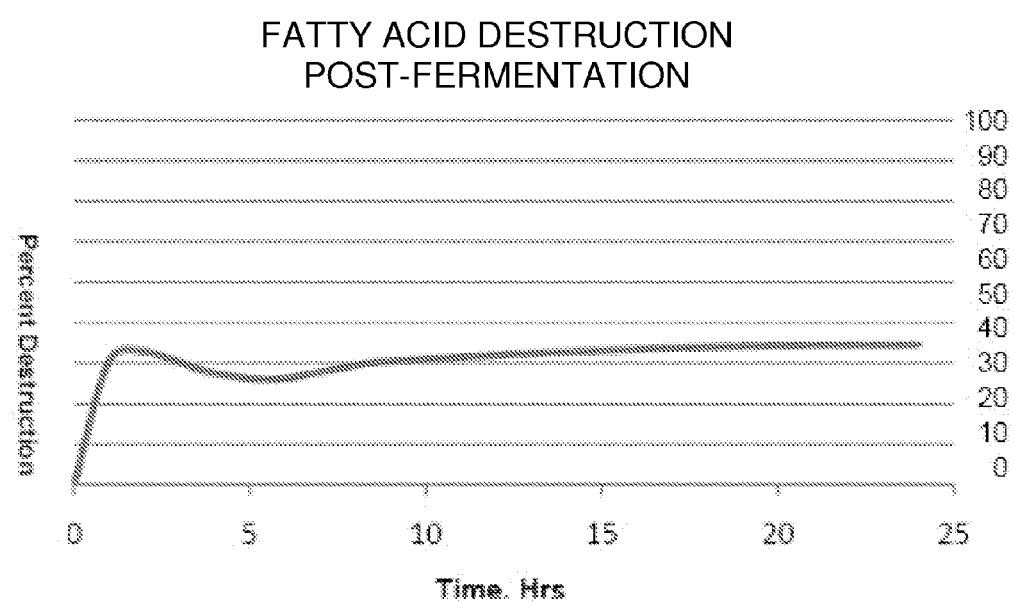
FIG. 5 is a graph of fatty acid destruction in corn feedstock as a function of time achieved through the use of post-fermentation lipase enzymes.

FIG. 4A is a graph of fatty acid destruction percentage in corn feedstock achieved through the use of pre-fermentation lipase enzymes. FIG. 4B is a graph of pre-fermentation fatty acid destruction in corn feedstock as a function of time. By way of contrast, FIG. 5 is a graph of post-fermentation fatty acid destruction as a function of time.

One purpose of the addition of the lipase at the front end of the process (pre-fermentation) is to destruct the fatty acids sufficiently to allow for the stillage to be employed post fermentation as a feed source to an anaerobic digestion system. Anaerobic digestion is hindered by the presence of the relatively high concentrations of fatty acids present in and natural to the corn and other feedstocks. Testing has shown that to effectively anaerobically digest stillage with high concentrations of fatty acids present (such as is in corn naturally), a catalyst has to be added, such as cattle manure, to initiate the digestion process. However, the addition of cattle manure drastically reduces post anaerobic digestion applications, such as cattle feed potential uses, e.g. dried distiller grains, or DDG's. The destruction of fatty acids within the scope of the present invention makes anaerobic digestion possible without any additional materials having to be added to the stillage prior to digestion. With no adulterants present during anaerobic digestion, it is possible to add the digestate to the wet distillers grain and produce dried distiller grains (DDG's). Lastly, the elimination of fatty acids allows for increased consumption of the DDG's to cattle as the fatty acids are the limiting factor in the health and wellness of cattle consuming the DDG's.

Currently known ethanol fermentation processes do not feed the stillage solid fraction to an anaerobic digester. This is due to contamination of the solids with naturally occurring fatty acids, namely, C-16:0, C-18:0, C-18:1, C-18:2, C-18:3, and C-20:0 fatty acids. One or more of these are toxic to the normal operating parameters of the anaerobic digester's bacterial degradation of the solids to methane. $E.\ coli$ bacteria are normally used, and high fatty acids, specifically oleic, when present in amounts greater than about 4% by weight, cause immediate toxicity to the bacteria.

The fatty acids may be destroyed by the addition of a specific decarboxylase enzyme to modify the organic acid function of the fatty acid, turning it into a long chain (C15-C17) conjugated and unconjugated linear analogs and free organic acids and alcohols or convertible to alcohols. In so doing, the oleic and other fatty acids are rendered harmless (non-toxic) to the biodigestion bacteria and in fact, are now able to be employed as potential feed stocks for methane production for the biodigester feed of the solid portion, thereby increasing the efficiency of the biodigester in reducing the organics to methane by simple anaerobic digestion. The enzymes may optionally be introduced in the recycled liquid fraction ("A" in FIG. 2).

The recycled liquid fraction ("A" in FIG. 2) may also be a carrier for a surfactant or surface active agent. As used herein, a surfactant is a compound specifically designed to lower the surface tension of the feedstock mash. The mash is the admixture of milled feedstock, such as corn, and water, such as recycled liquid from the thin stillage separation. Linear alkyl alkoxylates are non-limiting examples of suitable surfactants. The surfactant is preferably selected to be non-toxic to livestock and poultry so that stillage from the ethanol fermentation process may be used as animal feed, if desired. A consequence of this surfactant addition is several fold: 1) the liquid fraction penetrates into the smaller interstitial spaces of the feedstock mash. Whereas water cannot penetrate into dissolved or semi-solids at below 0.02 microns, the addition of the surfactant (surface active agent) makes this possible. 2) the surfactant has a viscosity reducing effect, whereby the addition of a surfactant to the feedstock mash makes the whole solution less viscous. 3) At the elevated temperature, the effect of the surfactant is to keep the solution mobile, that is, the surfactant increases the molecular ionic kinetics which increases reaction rates for enzyme and yeast fermentation reactions.

One useful benefit of surfactant addition is improved concentration of ethanol present in the fermenter effluent. The typical concentration of ethanol tends to be about 10-14% post fermentation, whereas employing this technology may allow for 18-20% ethanol concentrations. As the concentration of ethanol increases in the post fermentation step, the lower the cost per unit finished ethanol. Without being bound by theory, it is believed the increased ethanol concentration is possible due to the lowered osmotic pressure of the yeast cells in the fermentation process directly.

It will be understood that the surfactant may be added to the feedstock mash in any manner. If the thin stillage liquid fraction is recycled, a surfactant may be added to it. The surfactant may be added to water used to form the mash or it may be added directly to the mash.

One advantage to using the recycled liquid from the separation of the stillage is that the pH of the recycled liquid is at about 5.25±0.1 pH units and at temperature, 140-165° F., (60-73° C.). The temperature of the recycled liquid portion of the whole or thin stillage is at or near the desired optimum temperature for the enzyme reactions to take place. This is a suitable medium for the addition of enzymes specifically designed to destruct the cellulosic structures of the feedstock, such as corn.

It will be understood that enzymes may be added to the feedstock mash independent of the recycled liquid. Examples of enzymes that may be added include, but are not limited to, cellulase and hemicellulase. The cellulase specifically destructs the sugars present in the corn, such as the carbon 6 sugars, glucose, etc. and the hemicellulase is specific to the carbon 5 sugars present in a nearly equal amount in the corn. Both of these enzymes are from a similar source, and each is designed to destruct the cellulosics, C-6 and C-5 sugars by endo (cellulase, hemicellulase, following the peptidase analogy of exo and endo, whereby the glycosidic links are split in the middle of the polysaccharide) means, that is, from the middle of the cellulosic structure, not the non-reducing ends. Sub-group 3.2 includes true glycosides but also 3.2.2 enzymes hydrolyzing N-glycosyl compounds and 3.2.3.1 S-glycosyl compounds.

The feedstock is preferably subjected to the enzymatic destruction of the cellulosics prior to the thermal phase of the ethanol fermentation process. In so doing, the cellulose and the hemicelluloses are partially broken down thus giving rise to faster and easier destruction of the cellulosics during the fermentation phase of ethanol manufacturing. Further, by the addition of the hemicellulase, the C-5 sugars are partially destructed (and hydrolyzed) providing additional sugars to be converted to alcohol. Because corn contains roughly 50% cellulose and 50% hemicelluloses, additional alcohol may be produced from the hemicelluloses present in the corn. This step will lead to increased ethanol production from the additional hemicellulosic sugars partially hydrolyzed during the contact with the enzymes at the right temperature and pH.

It was noted that during the addition of the enzymes, both the cellulase and the hemicellulase, independently and together, gave a substantial reduction in the viscosity of the feedstock mash to the fermenter. This is contributory to the effects of the surfactant, discussed above, whereby the cumulative effect of the enzymes and the surfactant is highly synergistic.

Under conventional ethanol fermentation processes, the accepted value for the sugars that are fermentable is about 67% of the total sugars present. This is a theoretical yield and in practical applications, 45-55% of the total fermentable sugars are actually fermented, far lower than the amount actually present in the feedstock corn, for example. The other sugars present, pentosans, oligosaccharides, beta-glucans, dextrin, all for the most part are not considered to be fermentable via typical yeast fermentation. However, these compounds are not non-fermentable, but rather, non-digestible, a distinct but important difference.

Beta-glucans are digestible and fermentable after treatment with a beta-glucosidase. Similarly, oligosaccharides are fermentable after treatment with combinations of hemicellulase and alpha-amylase. Likewise, pentosans are fermentable after treatment with glucanase and xylanase.

The point here is pretreatment with appropriate enzymes may enhance ethanol production under a host of circumstances. For example, if the feedstock (corn, wheat, barley, switch grass, etc.) is identified and specified in the beginning, a cocktail of specific enzymes can be prepared to eliminate or at the very least, mitigate the structural differences of the feedstock to avail the yeast fermentation to proceed with these compounds in the feed mixture, readily available for digestion (partial or complete) prior to the fermentation cycle. The sugars representing the non-digestible entities are a major component in the additional ethanol produced from this process along with the reduced fatty acids which are converted to linear alcohols.

The actions of the enzymes are well established both from a specificity and performance review. Therefore, it is anticipated that additional enzymes can and will improve the yield of the ethanol using currently available yeasts by approximately 2 to 7.5%. New yeasts are under development which should improve the projected ethanol yield even more by approximately 7.5 to greater than 10%. The nature of these enzyme reactions are reproducible, but are not limited to corn based ethanol; they can be used with any of the anticipated varieties, switch grass, peanuts, wood, or any product capable of producing ethanol from simple fermentation processes. The makeup of the enzyme cocktail can be modified to be effective with the feedstock, no matter the feedstock composition, e.g. wood, switch grasses, peanuts, etc. The envisioned additional enzymes may be selected from, but are not limited to, pectinases, β-mannosidase, proteases, ligninases, and amylases specific to the individual problem based on the feedstock, e.g. corn, soybeans, peanuts, wood, switch grass, etc.

All the listed enzymes are commercially and readily available in bulk, relatively inexpensive and easy to use. This phase may be completely automated for automatic feed and can be monitored by flow, fluorometry and by a Shimadzu carbon, nitrogen and total oxidizable carbon automated detection system, calculating the dose of enzymes required based on flow, 90° nephelometry and carbon nitrogen ratios.

One useful benefit of reduced viscosity, whether by the use of surfactants, enzymes, or a combination of enzymes and surfactant, is improved concentration of ethanol present in the fermenter effluent, in addition to the improved yield of ethanol. Such improvement results from the lowered viscosity and the substantially reduced partially hydrolyzed polymeric hemicelluloses. The typical concentration of ethanol post fermentation may be increased up to 18-20% by employing part or all of the process improvements described herein. Without being bound by theory, it is believed the improved yield is attributable to the lowered osmotic pressure of the yeast cells in the fermentation process directly and the substantial hydrolysis of the polysaccharides into the short chain polymeric forms, (n=1, 2, 3, 4).

The following examples are given to illustrate various embodiments within the scope of the present invention. These are given by way of example only, and it is understood that the following examples are not comprehensive or exhaustive of the many types of embodiments of the present invention that can be prepared in accordance with the present invention.

EXAMPLE 1

The following non-limiting example is one of many possible implementations of the apparatus and method within the scope of the present invention. It illustrates possible energy savings resulting from separation and recycling of the liquid phase from whole or thin stillage and the use of solid phase from the whole or thin stillage in an anaerobic digester.

The liquid phase following fermentation and distillation processes has a temperature of about 60-70° C. (140-160° F.). The required energy to raise the temperature of fresh water consumed in the front end of the fermentation, is estimated at 123.8 million BTU (assuming a 100 gallon per minute influent water rate). The temperature to heat water is calculated in British thermal Units (BTU) where one BTU is described as the energy required to raise one pound of water, one degree Fahrenheit. Assuming an average temperature of the influent is 2.5-3.5° C. (36.5-41° F.). Raising the temperature to approximately 65° C. (or in Fahrenheit: 40° F. raised to 143° F.) on a theoretical 100 gallon per minute (gpm) plant this amounts to the 123.8 million BTU or 120,000 ft$^3$ of natural gas. By reusing (recycling) the clarified and heated liquid fraction from the separation of the whole or thin stillage, the consumption rate drops to 54 million BTU or 43.4%, saving 69.8 million BTU; this results in a savings of 68,000 ft$^3$ of natural gas, per day, assuming a 24 hour day.

Additional energy savings are available by using anaerobic digestion of solids from the thin or whole stillage. This is possible due to the enzymatic destruction of fatty acids in the feedstock described herein. The solids from the thin stillage and all or part of the whole stillage can be converted to methane using anaerobic bio-digestion. The above steps individually and collectively help to achieve the benefits described herein. The stillage is collected and fed to the digester. No additional additives are required as the pH is ideal for digestion at about 7.0 and the fatty acids are no longer present.

There is an estimated 3,000 (three thousand) BTU per pound of wet distillers grain when fed to an anaerobic bio-digester. The methane gas generated by this process may be fed to a piston engine-generator set. Methane engine generators range in efficiency from 40% to 55% conversion to electricity. The balance of the energy 40-55 percent of the waste heat is recaptured and utilized in the process.

TABLE 2

Calculations for Energy Conversion in Anaerobic Disgestion

Constants

300 GPM thin stillage stream
4.2% thin stillage solids content
100 BTU/percent stillage/pound
0.0002931 KW/BTU[1]
1.05 specific gravity[2]
8.345 lb/gallon[3]
55% efficient engine[4]
85% recapture of heat[5]
Electrical Generation = (300 gallons per minute)(8.345 pounds per gallon)(1.05)(1440 minutes per day)(100 BTU/#/%) (4.2%)
= [(300)(8.345)(1.05)(1440)(100)(4.2) BTU/day (0.0002931 KW/BTU)(0.55)]/24 Hr/day
= 10.7 MWH
Heat Recovery = [(300) (8.345) (1.05) (1440) (100) (4.2) BTU/day] (0.45) (.85)
= 608 MBTU per day

[1]Conversion of BTU to kilowatts
[2]Multiplier for weight conversion when mass is a factor
[3]Weight per unit volume
[4]GE Methane motor - generator
[5]Residual energy from electrical energy conversion process The separation process developed and described herein may provide the solid fraction to the anaerobic bio-digester at a density optimum to the specific digester. The density and volume of the slurry stream are proportional.

For example, the separation process designed for a 300 GPM thin stillage stream having a 4.2% solids content may be optimized to produce a 15% solids content. This would provide approximately 60 to 80 GPM solids feed to the digester. It would also provide approximately 220 to 240 GPM clear hot water available to be recycled.

The yield and efficiency of an ethanol fermentation process is improved by eliminating fatty acids present in the feedstock before fermentation of the feedstock. This enables the use of specific enzymes to hydrolyze selected "non-digestibles" and provides more fermentable sugars. The destruction of fatty acids also enables the stillage to be used more effectively as animal feed and permits stillage to be used in an anaerobic digester. An anaerobic digester can produce methane which can be used to generate electricity and heat for use in the ethanol fermentation process. Post anaerobic biodigestion solids may be available for addition as dried distillers grains (DDG's) if desired.

The yield and efficiency of an ethanol fermentation process is improved by adding one or more surfactants or surface active agents to the feedstock mash prior to fermentation. This improves penetrability of solids and semi-solids in the feedstock mash. As a result, enzymes (pre-fermentation) and yeast (during fermentation) show improved mass transfer and access of the enzyme to the substrate and of the yeast to fermentable sugars. In addition, it is believed the reduced osmotic pressure increases the maximum concentration of ethanol that can be produced during fermentation which further improves the yield and efficiency of the ethanol fermentation process.

The efficiency of an ethanol fermentation process is improved by recycling the heated water separated from the whole or thin stillage to the front end where it may be optionally mixed with enzymes and feed materials for the fermentation portion of the ethanol generation. The recycling of heated water reduces energy requirements for the process and it reduces the water fresh water requirements.

While specific embodiments of the present invention have been illustrated and described, numerous modifications come to mind without significantly departing from the spirit of the invention, and the scope of protection is only limited by the scope of the accompanying claims.

The invention claimed is:

1. A process for improving the yield and efficiency of an ethanol fermentation plant comprising:
   receiving fermentable corn-based feedstock material;
   destructing fatty acids present in the fermentable corn-based feedstock material prior to fermentation by adding one or more enzymes to the corn-based feedstock material, wherein the one or more enzymes are selected to destruct fatty acids present in the corn-based feedstock material and include a decarboxylase;
   fermenting the feedstock with yeast to produce ethanol;
   producing stillage as a by-product of ethanol fermentation;
   separating the stillage into thin stillage and wet distillers grain;
   directly introducing at least a portion of the wet distillers grain to an anaerobic digester to produce methane; and
   recovering digestate solids from the anaerobic digester as cattle feed.

2. The process according to claim 1, further comprising the step of adding one or more enzymes to the fermentable corn-based feedstock material prior to fermentation of the feedstock material, wherein the one or more enzymes is selected to destruct cellulose, hemicellulose, and lignin present in the feedstock, wherein the enzymes comprise a cellulase, a hemicellulase, and a ligninase.

3. The process according to claim 2, wherein the enzymes selected to destruct cellulose, hemicellulose, and lignin are selected from beta-glucosidases, alpha-amylase, glucanase, xylanase, pectinases, β-mannosidase, proteases, ligninases, amylases, and mixtures thereof.

4. The process according to claim 1, further comprising the steps of:
   separating a liquid fraction from the thin stillage comprising the steps of:
      adding a flocculant to the thin stillage, wherein the flocculant comprises an anionic polyacrylamide polymer having a molecular weight in range of about 8 to 25 million and having from about 25 to 50 mole percent anionic charge, said flocculant facilitating the formation of a solid fraction of the thin stillage;
recovering the solid fraction and the liquid fraction of the thin stillage; and
recycling the liquid fraction of the thin stillage to be combined with the fermentable feedstock.

5. The process according to claim 1, further comprising the step of adding a surfactant to the fermentable feedstock.

6. The process according to claim 5, wherein the surfactant comprises a linear alkyl alkoxylate.

7. The process according to claim 4, further comprising the step of adding a surfactant to the recycled liquid fraction.

8. A process for improving the yield and efficiency of an ethanol fermentation plant comprising:
receiving fermentable corn-based feedstock material;
destructing fatty acids present in the fermentable corn-based feedstock material prior to fermentation by adding one or more enzymes to the corn-based feedstock material, wherein the one or more enzymes are selected to destruct fatty acids present in the corn-based feedstock material and include a decarboxylase;
fermenting the feedstock with yeast to produce ethanol;
producing stillage, comprising a solid fraction of the stillage and thin stillage, as a by-product of ethanol fermentation;
separating a liquid fraction from the thin stillage comprising the steps of:
adding a flocculant to the thin stillage, wherein the flocculant comprises an anionic polyacrylamide polymer having a molecular weight in range of about 8 to 25 million and having from about 25 to 50 mole percent anionic charge, said flocculant facilitating the formation of a solid fraction of the thin stillage; and
recovering the solid fraction of the thin stillage and the liquid fraction of the thin stillage;
recycling the liquid fraction of the thin stillage to be combined with the fermentable feedstock, wherein from 70-85% of the total dissolved solids (TDS) are eliminated from the liquid fraction separated from the thin stillage, and wherein the liquid fraction comprises 700 mg/L or less total suspended solids (TSS); and
directly introducing a portion of the solid fraction of the thin stillage to an anaerobic digester to produce methane.

9. A process for improving the yield and efficiency of an ethanol fermentation plant comprising:
receiving fermentable corn-based feed stock material;
adding a decarboxylase to the fermentable corn-based feedstock material prior to fermentation of the feedstock material to destruct fatty acids present in the corn-based feedstock material;
adding one or more enzymes to the fermentable corn-based feedstock material prior to fermentation of the feedstock material, wherein the one or more enzymes is selected to destruct cellulose and hemicellulose present in the feedstock;
adding a surfactant to the fermentable corn-based feedstock, wherein the surfactant comprises a linear alkyl alkoxylate;
producing stillage as a by-product of ethanol fermentation comprising a solid fraction of the stillage and thin stillage;
separating a liquid fraction from the thin stillage component of the stillage comprising the steps of:
adjusting the thin stillage pH to a value in the range from 6 to 8.5;
adding a flocculant to the thin stillage, wherein the flocculant comprises an anionic polyacrylamide polymer having a molecular weight in range of about 8 to 25 million and having from about 25 to 50 mole percent anionic charge, said flocculant facilitating the formation of a solid fraction of the thin stillage;
recovering the solid fraction and the liquid fraction of the thin stillage; and
recycling the liquid fraction of the thin stillage to be combined with the fermentable feedstock; and directly introducing at least a portion of the solid fraction of the thin stillage, with no anaerobic digestion catalyst present, to an anaerobic digester to produce methane.

10. The process according to claim 9, wherein the one or more enzymes selected to destruct cellulose and hemicellulose present in the feedstock comprise a cellulase and a hemicellulase.

11. The process according to claim 10, wherein the enzymes selected to destruct cellulose and hemicellulose are selected from beta-glucosidases, alpha-amylase, glucanase, xylanase, pectinases, β-mannosidase, proteases, ligninases, amylases, and mixtures thereof.

12. The process according to claim 4, wherein the polyacrylamide polymer has a molecular weight in range of about 18 to 20 million.

13. The process according to claim 8, wherein the polyacrylamide polymer has a molecular weight in range of about 18 to 20 million.

14. The process according to claim 9, wherein the polyacrylamide polymer has a molecular weight in range of about 18 to 20 million.

15. The process according to claim 4, wherein the liquid fraction separated from the thin stillage comprises 700 mg/L or less total suspended solids (TSS).

16. The process according to claim 9, wherein the liquid fraction separated from the thin stillage comprises 700 mg/L or less total suspended solids (TSS).

17. The process according to claim 4, wherein from 70-85% of the total dissolved solids (TDS) are eliminated from the liquid fraction separated from the thin stillage.

18. The process according to claim 9, wherein from 70-85% of the total dissolved solids (TDS) are eliminated from the liquid fraction separated from the thin stillage.

19. The process according to claim 1, wherein no cattle manure is present in the portion of the wet distillers grain directly introduced to the anaerobic digester.

20. The process according to claim 8, wherein no anaerobic digestion catalyst is present in the portion of the solid fraction of the thin stillage directly introduced to the anaerobic digester.

* * * * *